United States Patent [19]

Breliere et al.

[11] Patent Number: 5,354,781
[45] Date of Patent: Oct. 11, 1994

[54] BENZENE DERIVATIVES, THEIR PREPARATION AND PHARMACEUTICAL COMPOSITIONS IN WHICH THEY ARE PRESENT

[75] Inventors: Jean-Claude Breliere; Pierre Casellas; Serge Lavastre, all of Montpellier; Raymond Paul, St Gely du Fesc, all of France

[73] Assignee: Sanofi, Paris, France

[21] Appl. No.: 707,229

[22] Filed: May 24, 1991

Related U.S. Application Data

[63] Continuation of Ser. No. 459,344, Dec. 29, 1989, abandoned.

[30] Foreign Application Priority Data

Dec. 30, 1988 [FR] France ............................ 88 17538

[51] Int. Cl.$^5$ .................... C07C 211/40; A61K 31/44
[52] U.S. Cl. ........................... 514/650; 564/338
[58] Field of Search ................... 564/338; 514/650

[56] References Cited

U.S. PATENT DOCUMENTS 4,104,383  8/1978  Krausz ................... 564/338

FOREIGN PATENT DOCUMENTS

| | | |
|---|---|---|
| 0040744 | 5/1981 | European Pat. Off. . |
| 0224163 | 11/1986 | European Pat. Off. . |
| 2451474 | 5/1975 | Fed. Rep. of Germany . |
| 1468761 | 8/1965 | France . |
| 2117942 | 7/1972 | France . |
| 2455889 | 12/1980 | France . |

OTHER PUBLICATIONS

Shafik et al., *J. Pharm. Sci.*, 68(6), pp. 776–780 (1979).
Mills et al. *J. Med. Chemi.*, 11, Jan. 1 1968, 95–97.

*Primary Examiner*—Glennon H. Hollrah
*Assistant Examiner*—Scott C. Rand
*Attorney, Agent, or Firm*—Bacon & Thomas

[57] ABSTRACT

The present invention relates to compounds of the formula

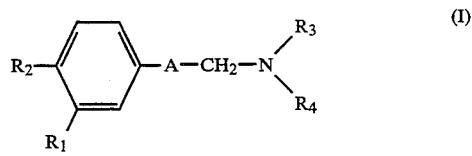

in which: p1 $R_1$ is hydrogen or a halogen atom;
$R_2$ is a cyclohexyl or a phenyl;
$R_3$ is a ($C_3$–$C_6$) cycloalkyl;
$R_4$ is hydrogen, ($C_1$–$C_6$) alkyl or ($C_3$–$C_6$)cycloalkyl;
A is —CO—$CH_2$—, —CH(Cl)—$CH_2$—, —CH(OH)—$CH_2$—, $CH_2$—$CH_2$—, —CH=CH— and —C≡C—, or their addition salt with mineral or organic acids. These compounds are active on the immune system. The present invention further relates to a method of preparing said compounds and to the pharmaceutical compounds in which they are present.

6 Claims, No Drawings

BENZENE DERIVATIVES, THEIR PREPARATION AND PHARMACEUTICAL COMPOSITIONS IN WHICH THEY ARE PRESENT

This application is a continuation of application Ser. No. 07/459,344, filed Dec. 29, 1989, now abandoned.

The present invention relates to novel benzene derivatives which are active on the immune system. It further relates to their preparation and to the pharmaceutical compositions in which they are present.

French patent 2 249 659 describes compounds of the formula

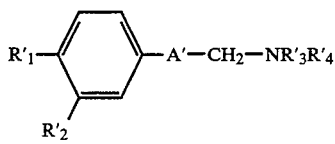

in which:
A' is the group —$CH_2$—$CH_2$— or —CH=CH—;
$R'_1$ is a cyclohexyl or a phenyl;
$R'_2$ is hydrogen or a halogen;
$R'_3$ is a hydrogen atom or a ($C_1$-$C_3$) alkyl group; and
$R'_4$ is a ($C_1$-$C_3$)alkyl group; or $R'_3$ and $R'_4$ can form a heterocyclic group when taken together with the nitrogen atom to which they are bonded.

According to said document, the compounds 1 have psychostimulant properties.

European patent application 224 163 describes compounds of the formula

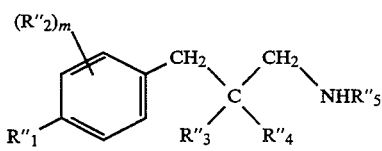

in which the various substituents can have the following meanings:
$R''_1$ and $R''_2$ are a hydrogen, an alkyl, a cycloalkyl or a halogen;
$R''_3$ and $R''_4$ are hydrogen or an alkyl; and
$R''_5$ is an alkyl or a cycloalkyl.

Most of the compounds described in the Examples of said patent application have formula 2 in which $R''_1$=tert-$C_4H_9$, $R''_3$=H and $R''_4$=$CH_3$.

Said patent application does not describe any compounds in which the substituents $R''_2$, $R''_3$ and $R''_4$ have the following meanings: $R''_3$ and $R''_4$=H and/or $R''_2$=cycloalkyl or phenyl.

According to the description of said patent, the compounds described have a fungicidal activity on phytopathogenic fungi.

According to the present invention, a novel family of benzene derivatives have now been found which possess unexpected properties: in fact, these compounds have valuable properties in the immune system.

The present invention relates to compounds of the formula

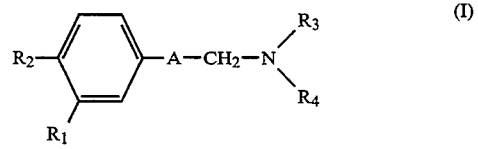

in which:
$R_1$ is a hydrogen atom or a halogen atom;
$R_2$ is a cyclohexyl or a phenyl;
$R_3$ is a cycloalkyl containing from 3 to 6 carbon atoms;
$R_4$ is a hydrogen atom, an alkyl containing from 1 to 6 carbon atoms or a cycloalkyl containing from 3 to 6 carbon atoms; and
A is a group selected from: —CO—$CH_2$—, —CH(Cl)—$CH_2$—, —CH(OH)—$CH_2$—, —$CH_2$—$CH_2$—, —CH=CH— and —C≡C—,
and to their addition salts with mineral or organic acids.

According to the invention, halogen atom is understood as meaning fluorine, chlorine, bromine or iodine atoms, the chlorine atom being preferred.

Of the cycloalkyls, cyclohexyl is a preferred group.

Thus the compounds (I) in which $R_1$ is a chlorine atom and $R_2$ and $R_3$ are each a cycloalkyl are particularly preferred.

When A is a vinylene group, the compounds (I) of cis and trans configurations form an integral part of the invention.

When A is a chlorethylene or hydroxyethelene group, the compounds (I) have an asymmetric carbon atom. The racemates and the optically active isomers of these compounds form an integral part of the invention.

The salts of the compounds of formula (I) according to the present invention include those with mineral or organic acids which enable the compounds of formula (I) to be suitably separated or crystallized, such as picric acid, oxalic acid or an optically active acid, for example a mandelic acid or a camphorsulfonic acid, as well as those which form pharmaceutically acceptable salts such as the hydrochloride, the hydrobromide, the succinate, the sulfate, the bisulfate, the dihydrogenphosphate, the methanesulfonate, the methylsulfate, the acetate, the benzoate, the citrate, the glutamate, the maleate, the fumarate, the p-toluenesulfonate and the naphthalene-2-sulfonate.

The present invention further relates to a method of preparing the compounds (I).

This method comprises:

a) carrying out a condensation reaction of formaldehyde and an amine of the formula $HNR_3R_4$, in which $R_3$ and $R_4$ are as defined above for (I), either with the acetophenone of the formula

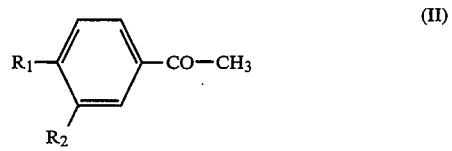

in which $R_1$ and $R_2$ are as defined above for (I), to give a compound (I) according to the invention in which A is the group —CO—$CH_2$—, or with a phenylacetylenic derivative of the formula

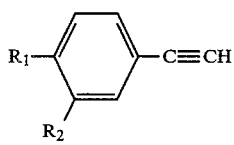

in which $R_1$ and $R_2$ are as defined above, to give a compound (I) according to the invention in which A is the group —C≡C—;

b) if appropriate, reacting a reducing agent with the compound (I) in which A is a group —CO—$CH_2$— in order to prepare the compound (I) according to the invention in which A is a group —CHOH—$CH_2$—;

c) if appropriate, reacting a chlorinating agent with the compound (I) in which A is —CHOH—$CH_2$—, in an inert solvent, in order to prepare the compound (I) according to the invention in which A is —CHCl—$CH_2$—;

d) if appropriate, carrying out a hydrogenation of the compound (I) in which A is the acetylenic group —C≡C—, with nascent hydrogen, in order to prepare the compound (I) in which A is the group —CH=CH—, in the form of a mixture of the cis and trans isomers, or carrying out a hydrogenation in the presence of a supported metal catalyst in order to prepare the ethylenic compound (I) in the cis form, or dehydrating the compound (I) in which A is a group —CHOH—$CH_2$— in order to prepare the ethylenic compound (I) in the trans form;

e) if appropriate, carrying out a hydrogenation of the compound (I) in which A is a group —CH=CH— or a group —C≡C— in order to prepare the compound (I) according to the invention in which A is the group —$CH_2$—$CH_2$—; and f) finally, if necessary, preparing an addition salt of a compound (I) by the addition of an appropriate mineral or organic acid.

The starting acetophenones (II) are known or are prepared by known methods such as those described in Gazz. Chim. Ital. 1949, volume 79, 453–457, and J. Am. Chem. Soc. 1947, volume 69, 1651–1652. Likewise the amines $HNR_3R_4$ are known and are commercially available.

When the condensation reaction of step a) of the method according to the invention is carried out on the acetophenone (II), it is performed in an acid medium in a solvent such as alcohol or dimethoxyethane.

In particular, the phenylacetylenic derivative (III) can be obtained from the acetophenone (II) by first preparing a chlorophenylethylenic derivative of the formula

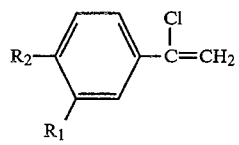

by reaction of phosphorus pentachloride with the acetophenone (II) and hydrolysis, and then by dehydrohalogenating the compound (IV) in a basic medium.

Starting from the acetophenone (II), it is also possible to prepare an intermediate semicarbazone (V) and then apply the procedure described by I. LALEZARI et al. (Angew. Chem., Internat. Ed., 1970, 9(6), p. 464) by reacting said intermediate with selenium oxide under the action of heat, in an acid medium, and then decomposing the intermediate selenodiazole (VI) formed, under the action of heat, to give the phenylacetylenic derivative (III) according to the following reaction scheme:

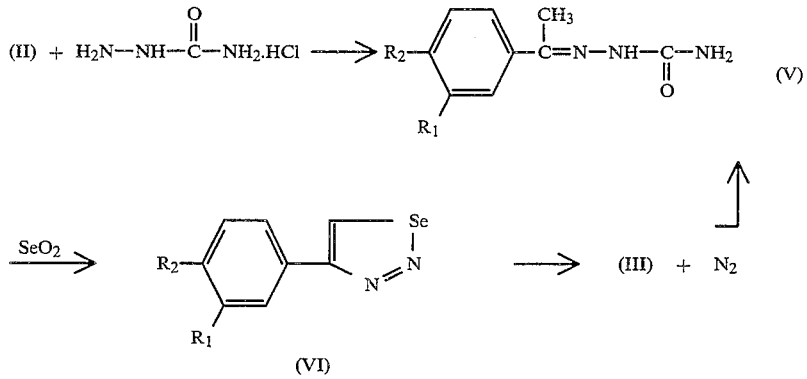

When step a) of the method according to the invention is carried out on the phenylacetylenic derivative (III), it is performed under the action of heat, in an inert solvent such as dioxane or dimethoxyethane; to facilitate the condensation reaction, it is possible to use a metal salt, such as cuprous chloride or cuptic chloride, as a catalyst.

In step b) of the method, the reducing agent is preferably a metal hydride, for example sodium borohydride, and the reaction is preferably carried out in an alcoholic solvent at a temperature below 10° C.

In step c), it is possible to use a chlorinating agent such as thionyl chloride, phosgene or, for example, a phosphorus chloride such as phosphorus oxychloride or phosphorus pentachloride.

The reaction is carried out under the action of heat, in a solvent such as chloroform or dichloroethane.

In step d) of the method, the hydrogenation with nascent hydrogen can be carried out by reaction with zinc in acetic acid, or the dehydrating agent is, for example, p-toluenesulfonic acid used in toluene, at the reflux temperature of the medium, or, when the hydrogenation is carried out in the presence of a supported metal catalyst such as palladium on barium sulfate or on calcium carbonate, or Raney nickel, in a wholly or partly alcoholic solvent, it can be performed in the presence of quinoline to facilitate the reaction; the catalytic hydrogenation effected in this way yields only compounds (I) of cis configuration (Catalytic Hydrogenation—R. L. Augustine—New York: Marcel Dekker, 1965, p. 69–71).

In step e) of the method, the reaction can be carried out in the presence of a catalyst, for example platinum oxide.

The product of formula (I) is isolated, in the form of the free base or a salt, according to the conventional techniques.

When the compound of formula (I) is obtained in the form of the free base, salt formation is effected by treatment with the chosen acid in an organic solvent. Treatment of the free base, for example dissolved in an alcohol such as isopropanol, with a solution of the chosen acid in the same solvent gives the corresponding salt, which is isolated according to the conventional techniques. Examples of salts prepared in this way are the hydrochloride, the hydrobromide, the sulfate, the bisulfate, the dihydrogenphosphate, the methanesulfonate, the methylsulfate, the oxalate, the maleate, the fumarate and the naphthalene-2-sulfonate.

When the reaction is complete, the compound of formula (I) can be isolated in the form of one of its salts, for example the hydrochloride or the oxalate; in this case, if necessary, the free base can be prepared by neutralization of said salt with an inorganic or organic base such as sodium hydroxide or triethylamine, or with an alkali metal carbonate or bicarbonate such as sodium or potassium carbonate or bicarbonate.

The compounds of the present invention were subjected to immunosuppressive activity tests. In particular, they were studied in vivo on an experimental model of autoimmune thyroiditis in mice, induced by porcine thyroglobulin (PTg) according to J. Salamero et al., Eur. J. Immunol., 1987, 17, 843–848. The level of antibodies directed against porcine thyroglobulin was measured by the ELISA method (enzyme-linked immunosorbent assay) after 20 consecutive days of treatment. It was observed that the compounds according to the invention induce a distinct decrease in antibody production in the animals treated.

The compounds of formula (I) have a low toxicity; in particular, their acute toxicity is compatible with their use as drugs in areas of therapy where it is desirable to reduce the immunological activity. The following may be mentioned by way of indication and without implying a restriction: diseases with an autoimmune component, for example rheumatoid polyarthritis, lupus erythematosus, multiple sclerosis and diabetes, or graft rejection reactions, graft versus host reaction, organ transplant situations (liver, kidney, heart, pancreas, bone marrow) and psoriasis.

For such a use, an effective amount of a compound of formula (I) or one of its pharmaceutically acceptable salts is administered to mammals needing said treatment.

Cis-N-cyclohexyl-N-ethyl-3-(3-chloro-4-cyclohexylphenyl)prop-3-enylamine and its pharmaceutically acceptable salts, especially the hydrochloride, are particularly preferred.

The compounds of formula (I) above and their pharmaceutically acceptable salts can be used in daily doses of 0.01 to 100 mg per kilogram of body weight of the mammal to be treated, preferably in daily doses of 0.1 to 50 mg/kg. In humans, the dose can vary preferably from 0.5 to 4000 mg per day, more particularly from 2.5 to 1000 mg, depending on the age of the subject to be treated or the type of treatment: prophylactic or curative.

The compounds of formula (I) are generally administered in dosage units. Said dosage units are preferably formulated as pharmaceutical compositions in which the active principle is mixed with a pharmaceutical excipient.

Thus, according to another of its features, the present invention relates to pharmaceutical compositions in which at least one of the compounds of formula (I) or one of its pharmaceutically acceptable salts is present as the active principle.

In the pharmaceutical compositions of the present invention for oral, sublingual, subcutaneous, intramuscular, intravenous, percutaneous or rectal administration, the active principles can be administered to animals and humans in the form of administration units, mixed with the conventional pharmaceutical excipients. The appropriate unit forms of administration include forms for oral administration, such as tablets, capsules, powders, granules and solutions or suspensions to be taken orally, forms for sublingual and buccal administration, forms for percutaneous, subcutaneous, intramuscular or intravenous administration and forms for rectal administration.

Each unit dose can contain from 0.5 to 1000 mg, preferably from 2.5 to 200 mg, of active ingredient, combined with a pharmaceutical excipient. This unit dose can be administered 1 to 4 times a day.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose or other appropriate substances or they can be treated so as to have a sustained or delayed activity and so as to release a predetermined amount of active principle continuously.

A preparation in the form of gelatin capsules is obtained by mixing the active ingredient with a diluent and pouring the mixture obtained into soft or hard gelatin capsules.

Water-dispersible powders or granules can contain the active ingredient mixed with dispersants, wetting agents or suspending agents such as polyvinylpyrrolidone, as well as with sweeteners or taste correctors.

Rectal administration is carried out using suppositories, which are prepared with binders melting at the rectal temperature, for example cacao butter or polyethylene glycols.

Parenteral administration is carried out using aqueous suspensions, isotonic saline solutions or sterile and injectable solutions which contain pharmacologically compatible dispersants and/or wetting agents, for example propylene glycol or butylene glycol.

A preparation in the form of a syrup or an elixir can contain the active ingredient in combination with a sweetener, which is preferably calorie-free, methylparaben and propylparaben as antiseptics, a flavoring agent and an appropriate colorant.

The active principle can also be formulated as microcapsules, with one or more excipients or additives if desired.

The present invention further relates to the pharmaceutical compositions in which at least one of the compounds of formula (I) or one of its pharmaceutically acceptable salts is present in association with another active principle. Examples of other active principles which may be chosen are an immunosuppressant, a cytostatic agent or an antimetabolite such as, in particular, ciclosporin, azathioprine, methotrexate, cyclophosphamide or chlorambucil. An anti-rejection monoclonal antibody, for example an anti-CD3 antibody, may also be administered in association with a compound of formula (I) or one of its pharmaceutically acceptable salts.

The following Examples illustrate the invention without implying a limitation.

EXAMPLE 1

N-Cyclohexyl-N-methyl-3-(3-chloro-4-cyclohexyl-phenyl)prop-2-ynylamine hydrochloride. CM 31739

A) 3-Chloro-4-cyclohexyl-1-ethynylbenzene 129 g of phosphorus pentachloride are added in small portions, over 30 minutes, to 118.3 g of 3-chloro-4-cyclohexylacetophenone. The temperature is raised gradually to 105° C. over one hour and the mixture is then heated at this temperature for 1 and a half hours and at 115° C. for a further 1 and a half hours. The gum formed is extracted with ethyl ether and the ether phase is washed with 5% sodium hydroxide solution, dried and concentrated to give 107 g of 3-chloro-4-cyclohexyl-α-chlorostyrene. This product is dissolved in 450 ml of ethanol and the solution is then refluxed for 24 hours in the presence of 94 g of potassium hydroxide. The bulk of the alcohol is concentrated and replaced with water, extraction is carried out with ethyl ether and the ether phase is dried and concentrated to give 72.5 g of crude product. 41.7 g of a liquid are obtained after distillation under reduced pressure.

Boiling point: 102°–104° C. under 4 mm of mercury (=533 Pa).

B) CM 31739.

A solution containing 16.4 g of 3-chloro-4-cyclohexyl-1-ethynylbenzene, prepared above, in 30 ml of dioxane, 4.5 g of paraformaldehyde and 0.15 g of cuprous chloride is heated to 60° C. and 9.3 g of N-methyl-N-cyclohexylamine are then added over half an hour. The temperature is kept at 60° C. for 1 hour. When the reaction is complete, the cooled mixture is diluted with ether and treated with water and then with a dilute solution of hydrochloric acid. The acid solution is then rendered alkaline with a dilute solution of sodium hydroxide and extracted with ether. The organic phase is dried over sodium sulfate and then concentrated. The hydrochloride is prepared from the crude base, washed with water and then crystallized twice from acetonitrile to give 8.4 g of the expected compound.

M.p.: 175° C.

EXAMPLE 2

Cis-N-cyclohexyl-N-methyl-3-(3-chloro-4-cyclohexyl-phenyl)prop-3-enylamine hydrochloride. CM 31748.

A solution containing 13.1 g of the compound prepared in Example 1, in the form of the base, and 1.2 g of 5% palladium on barium sulfate in 100 ml of ethyl acetate and 5 ml of methanol is hydrogenated at normal temperature and pressure. The volume of hydrogen absorbed is 650 ml. After filtration and concentration of the solution, the residue is taken up in ethyl ether and the hydrochloride is precipitated by bubbling hydrogen chloride. 5.6 g of the expected compound are obtained after recrystallization from acetonitrile.

Yield: 43%.

The NMR spectrum of this compound was run at 60 MHz in dimethyl sulfoxide.

| Chemical shift (ppm) | Appearance | Integration | Assignment |
|---|---|---|---|
| between 0.75 and 3.5 | unresolved signals | 25 H | 2 cyclohexyl NCH$_3$ |
| 3.85 | multiplet | 2 H | CH$_2$—N |
| 6.2 Jcis = 11 Hz JCH—CH$_2$ = 6 Hz | doublet of triplets | 1 H | —CH═CH—CH$_2$—N |
| between 6.5 and 7.5 | unresolved signals | 4 H | 3H (aromatic) —CH═CH—CH$_2$— |

EXAMPLE 3

Cis- and trans-N-cyclohexyl-N-methyl-3-(3-chloro-4-cyclohexylphenyl)prop-2-enylamine hydrochloride.

A solution containing 6 g of CM 31739, prepared in Example 1, and 6 g of zinc in 100 ml of acetic acid and 70 ml of water is refluxed for one hour. After cooling, concentrated sodium hydroxide solution is added and the mixture is then extracted with ethyl ether. The ether phase is washed with water, dried over sodium sulfate and then concentrated to give 5.2 g of product. The hydrochloride is prepared by the addition of hydrochloric acid in ethyl ether and washed with acetone. 2.8 g of the cis isomer are collected as a precipitate. The filtrate is concentrated and 1.3 g of the trans compound (CM 31751) are then obtained after crystallization from acetone and recrystallization from acetonitrile.

Melting point: 198° C.

The NMR spectrum of the trans compound is run at 60 MHz in dimethyl sulfoxide.

| Chemical shift | Appearance | Integration | Assignment |
|---|---|---|---|
| between 0.9 and 3.4 | unresolved signals | 25 H | 2 cyclohexyl N—CH$_3$ |
| 3.75 | multiplet | 2 H | —CH$_2$—N |
| 6.55 | multiplet | 2 H trans | H\\C═C\\H |
| between 7 and 7.5 | unresolved signals | 3 H | H (aromatic) |

EXAMPLE 4

N-Cyclohexyl-N-ethyl-3-(3-chloro-4-cyclohexyl-phenyl)prop-2-ynylamine hydrochloride. CM 31738

A) 3-Chloro-4-cyclohexylacetophenone semicarbazone 73.59 g of semicarbazide hydrochloride and 54.12 g of sodium acetate are dissolved in 600 ml of distilled water. After the mixture has been stirred, a solution of 142 g of 3-chloro-4-cyclohexylacetophenone in 600 ml of ethanol is added rapidly at room temperature. The mixture is heated at 50° C. for 2 hours and then stirred at room temperature overnight. The crystals formed are filtered off, washed with water, acetone and then ethyl ether and dried under vacuum to give 169.50 g of white crystals of the semicarbazone.

Yield: 96%.

Rf (methylene chloride/methanol: 95/5): 0.4.

The structure of the semicarbazone is confirmed by analysis of the NMR spectrum.

B) 3-Chloro-4-cyclohexyl-1-ethynylbenzene

A suspension of 26 g of finely ground selenium oxide and 58.7 g of the semicarbazone obtained in the previous step is prepared in 400 ml of glacial acetic acid. It is heated by means of an oil bath at 60° C. for 1 hour and then at 80° C. for 2 hours to form the intermediate selenodiazole. The temperature of the oil bath is raised to 150° C. for 3 and a half hours until the selenodiazole has completely decomposed and the evolution of nitrogen has ceased. The acetic acid is evaporated off under vacuum, the residue is taken up with 600 ml of ether, the mixture is filtered to remove the precipitated selenium and the filtrate is washed 4 times with water, once with a 5% aqueous solution of sodium hydroxide and twice with water. It is dried over sodium sulfate and potassium carbonate and evaporated under vacuum and the oily residue is then distilled under 0.01 mm of mercury (1.33 Pa) to give 24.8 g of a colorless oil.

Yield: 57%.

C) CM 31738.

A solution containing 13.46 g of the compound prepared in the previous step and 0.25 g of cuptic chloride in 50 ml of dimethoxyethane is stirred at room temperature. A mixture containing 9 g of 35% aqueous formaldehyde and 9.42 g of N-ethyl-N-cyclohexylamine in 35 ml of dimethoxyethane is added dropwise. The mixture is heated at 70° C. for 1 hour 15 minutes and the solvent is then evaporated off under vacuum. The residue is taken up in ether and the mixture is washed with a 5% aqueous solution of sodium hydroxide, washed with water and then dried over sodium sulfate and concentrated to dryness. The hydrochloride is formed by the addition of hydrochloric acid in anhydrous ether, filtered off, washed with ethyl ether and dried. The solid formed is dissolved in methylene chloride and the solution is washed twice with water to remove the unreacted N-ethyl-N-cyclohexylamine, and then dried and concentrated under vacuum. The residue obtained is crystallized from an acetone/ether mixture to give 22.7 g of white crystals.

Yield: 93%.

Melting point: 169° C.

The structure of the compound is confirmed by analysis of the NMR spectrum.

EXAMPLE 5

Cis-N-cyclohexyl-N-ethyl-3-(3-chloro-4-cyclohexylphenyl)prop-2-enylamine hydrochloride. CM 31747

18.1 g of the compound obtained in Example 4, in the form of the free base, are dissolved in 140 ml of ethyl acetate and 5 ml of methanol. Hydrogenation is carried out, under atmospheric pressure, in the presence of 0.9 g of 5% palladium on barium sulfate. The hydrogenation is stopped after 1 hour 40 minutes and the volume of hydrogen absorbed is 1.24 liters. The catalyst is filtered off and the solvent is evaporated off to give 17 g of crude product. This is chromatographed on 250 g of silica using a methylene chloride/methanol mixture (97/3) as the eluent to give 14 g of the free base, which crystallizes in the form of hydrochloride from ethyl ether. After filtration and drying, 12.22 g of the expected compound are obtained in the form of the hydrochloride.

Yield: 61%.

Melting point: 192° C.

The structure of the compound is confirmed by analysis of the NMR spectrum.

EXAMPLE 6

N,N-Dicyclohexyl-3-(3-chloro-4-cyclohexylphenyl)-prop-2-ynylamine hydrochloride. CM 31740.

This compound is prepared, following the procedure described in Example I, by reacting dicyclohexylamine and paraformaldehyde with 3-chloro-4-cyclohexyl-1-ethynylbenzene.

Melting point: 165° C.

EXAMPLE 7

Cis-N,N-dicyclohexyl-3-(3-chloro-4-cyclohexylphenyl)prop-2-enylamine hydrochloride. CM 31750

This compound is prepared, following the procedure described in Example 2, from the CM 31740 prepared in Example 6, in the form of the base.

Melting point: 166° C.

EXAMPLE 8

N-Cyclohexyl-N-ethyl-3-(3-chloro-4-cyclohexylphenyl)propylamine hydrochloride. SR 45596 A This compound is obtained from the CM 31738 prepared in Example 4.

4 g of the hydrochloride prepared in Example 4 are dissolved in 1 ml of methanol and 28 ml of ethyl acetate, and 0.18 g of palladium on barium sulfate is added.

The reaction medium is placed under a hydrogen atmosphere for 7 hours, the catalyst is then filtered off and the medium is concentrated to dryness under vacuum. The residue is taken up with methylene chloride and chromatographed on a silica column using a methylene chloride/methanol mixture (93/7 v/v, then 90/10 v/v) as the eluent.

After evaporation, the oil obtained is diluted in ether and the salt then crystallizes on the addition of hydrochloric acid in ether. 1.5 g of product are obtained.

Melting point: 165° C.

EXAMPLE 9

1-(3-Chloro-4-cyclohexylphenyl)-3-(N-cyclohexyl-N-ethylamino)propan-1-one hydrochloride. SR 46232 A 23.6 g of 3-chloro-4-cyclohexylacetophenone, 16.3 g of N-cyclohexyl-N-ethylamine hydrochloride, 6 g of paraformaldehyde and 3.5 ml of hydrochloric acid are refluxed in 200 ml of dimethoxyethane for 18 hours. The solvent is evaporated off and the residue is taken up with 700 ml of ethyl ether. The solid obtained is taken up with methylene chloride, the mixture is washed with water and filtered and the filtrate is dried over sodium sulfate. The yellow oil obtained is taken up with 500 ml of ethyl acetate to give 21.5 g of a white solid in the form of crystals.

Melting point: 154°–156° C.

EXAMPLE 10

1-(3-Chloro-4-cyclohexylphenyl)-3-(N-cyclohexyl-N-ethylamino)propan-1-ol hydrochloride. SR 46233 A 4.12 g of the propanone prepared in the previous Example in 100 ml of methanol are cooled to 4° C. 0.13 g of sodium borohydride is added in portions, the mixture being kept at a temperature of between 5° and 10° C. for 30 minutes and then being allowed to return to room temperature over 1 hour. The methanol is evaporated off, the residue is taken up with water and then extracted with ethyl acetate and the organic phase is dried over sodium sulfate. The hydrochloride is prepared by the addition of hydrogen chloride. The white solid which crystallizes is washed with ether to give 3.23 g of the expected product.

Melting point: 165°–167° C.

EXAMPLE 11

3-Chloro-3-(3-chloro-4-cyclohexylphenyl)-N-cyclohexyl-N-ethylpropylamine hydrochloride. SR 46264

A mixture containing 6.2 g of the compound prepared in the previous Example and 6.3 g of thionyl chloride in 150 ml of chloroform is heated to the reflux temperature. After 20 minutes, the evolution of gas ceases, the reaction medium is evaporated, the oily residue is washed with acetone, and 150 ml of ethyl acetate are then added. The expected product crystallizes to give 5.8 g.

Melting point: 174°–176° C.

EXAMPLES 12 AND 13

The following compounds are prepared by using the methods disclosed respectively in Examples 9 and 10:

1-(3-chloro-4-cyclohexylphenyl)-N-cyclohexyl-3-amino-propan-1-one oxylate Melting point: 181°–183° C.

1-(3-chloro-4-cyclohexylphenyl)-N-cyclohexyl-3-amino-propan-1-ol hydrochloride Melting point: 264°–2660° C.

EXAMPLE 14

| Preparation of capsules | |
|---|---|
| CM 31747 | 25 mg |
| Lactose | 110 mg |
| Magnesium stearate | 5 mg |

What is claimed is:

1. Cis-N-cyclohexyl-N-ethyl-3-(3-chloro-4-cyclohexylphenyl)prop-2-enylamine or one of its pharmaceutically acceptable addition salts.

2. Cis-N-cyclohexyl-N-ethyl-3-(3-chloro-4-cyclohexylphenyl)prop-2-enylamine hydrochloride.

3. A pharmaceutical composition comprising as active principle an effective amount of a compound according to claim 1, together with a pharmaceutically acceptable excipient.

4. A pharmaceutical composition according to claim 3 which is in the form of a dosage unit in which the active principle is mixed with a pharmaceutically acceptable excipient.

5. A pharmaceutical composition according to claim 4 which contains from 0.5 to 1000 mg of active principle per dosage unit.

6. A pharmaceutical composition according to claim 5 which contains from 2.4 to 200 mg of active principle per dosage unit.

* * * * *